United States Patent [19]

Crowe et al.

[11] Patent Number: 4,857,319

[45] Date of Patent: Aug. 15, 1989

[54] METHOD FOR PRESERVING LIPOSOMES

[75] Inventors: John H. Crowe; Lois M. Crowe, both of Davis, Calif.

[73] Assignee: The Regents of the University of California, Berkeley, Calif.

[21] Appl. No.: 52,795

[22] Filed: May 21, 1987

Related U.S. Application Data

[63] Continuation-in-part of Ser. No. 690,679, Jan. 11, 1985, abandoned.

[51] Int. Cl.$^4$ .................. A61K 37/24; A61K 37/48
[52] U.S. Cl. .................. 424/94.1; 424/94.4; 514/2; 514/3; 514/76; 514/77; 514/78; 514/44; 514/579; 514/646; 435/4; 435/26; 436/829
[58] Field of Search .................. 424/450, 94.1, 94.4; 514/76–78, 2, 3; 435/4; 436/829

[56] References Cited

U.S. PATENT DOCUMENTS 3,993,754 11/1976 Rahman et al. .
4,016,100 4/1977 Suzuki et al. .
4,224,179 9/1980 Schneider .
4,229,360 10/1980 Schneider et al. .
4,235,871 11/1980 Papahadjopoulos et al. .
4,263,428 4/1981 Apple et al. .
4,348,384 9/1982 Horikoshi et al. .
4,370,349 1/1983 Evans et al. .
4,396,630 8/1983 Riedl et al. .
4,411,894 10/1983 Schrank et al. .
4,515,736 5/1985 Deamer .

FOREIGN PATENT DOCUMENTS

86/01103 2/1986 World Int. Prop. O. .

OTHER PUBLICATIONS

Szoka et al., *Ann. Rev. Biophysics Bioeng.* 9:467–508 (1980).
*Chem. Abs.* 97:11851g (1982).
*Chem. Abs.* 99:163956z (1983).
Crowe et al., *Archives of Biochemistry and Biophysics,* vol. 220, (1983), pp. 477–484.
Tsyganenko et al., *Antibiotiki,* 28(8), 1983, pp. 577–581 (Russ.)
*Chem. Abs.* 101:216308h (1984).
*Archives of Biochemistry and Biophysics,* vol. 232, No. 1, Jul. 1984, pp. 400–407.
Crommelin et al., *Pharmaceutical Research,* No. 3, (1984), pp. 159–163.
Crowe et al., *Biochimica et Biophysica Acta* 769, (1984), pp. 141–150, 151–159.
E. Racker, "Reconstruction of Cyrochrome Oxidase Vesicles and Conferral of Sensitivity to Energy Transfer Inhibitors", *J. Membrane Biol.,* 10, 221–235 (1972).

*Primary Examiner*—Sam Rosen
*Attorney, Agent, or Firm*—Majestic, Parsons, Siebert & Hsue

[57] ABSTRACT

A method for preserving liposomes includes freeze-drying liposomes most preferably having an average size of about 50 nm to 100 nm with a disaccharide preserving agent being present both internally (with the encapsulated liposomal contents) and externally. The disaccharide component is in a weight ratio with respect to the lipid component of from at least about 0.1:1 to not greater than about 4:1 and is preferably trehalose. When the lyophilizates are reconstituted by rehydration, the resultant liposomes can retain up to 100% of the originally encapsulated contents.

14 Claims, 4 Drawing Sheets

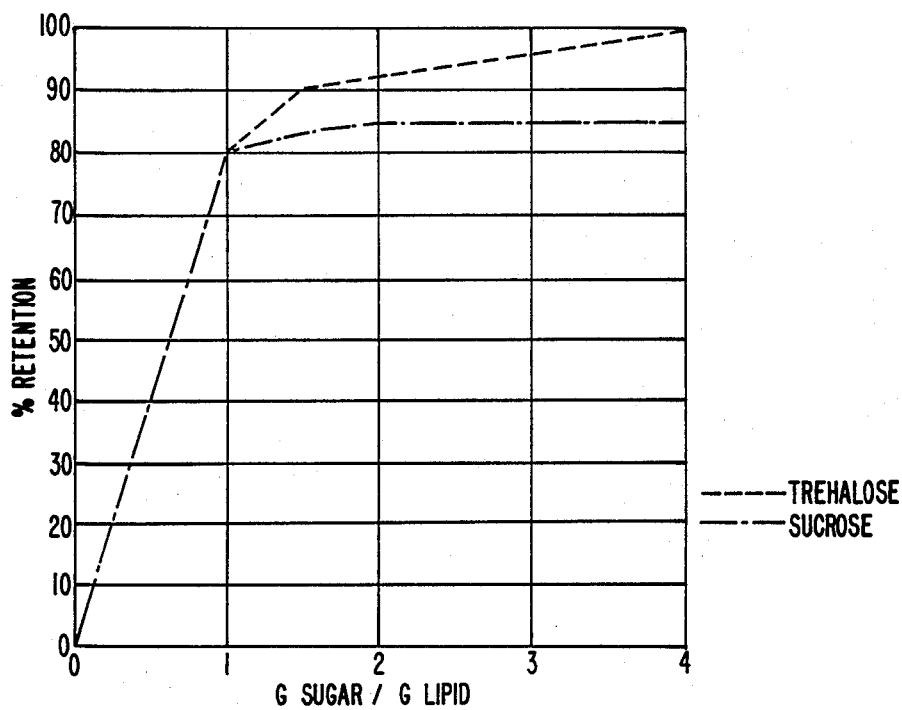
FIG._1.
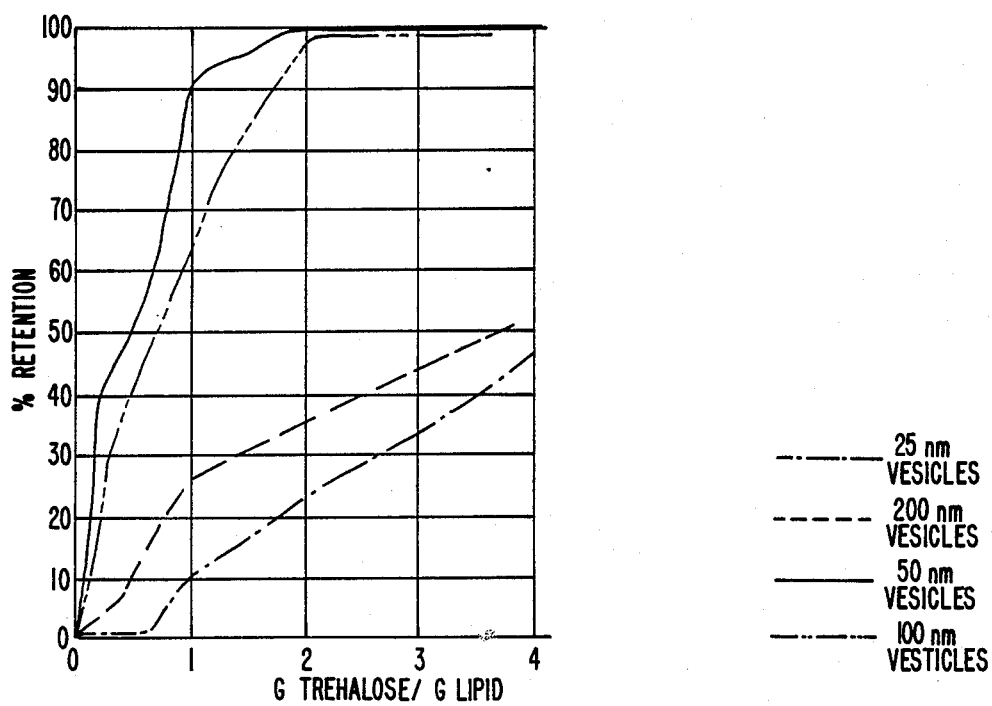
FIG._2.

FIG._3.
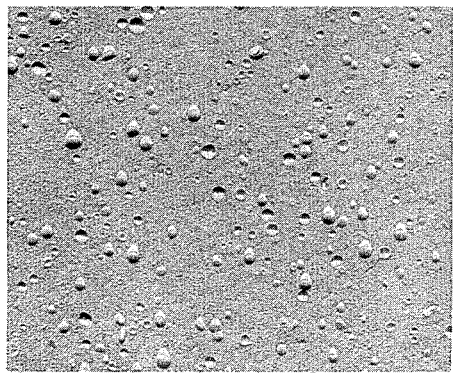
FIG._4.
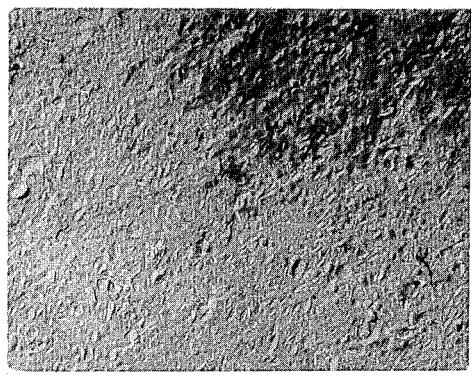

METHOD FOR PRESERVING LIPOSOMES

This invention was made with Government support under Grant No. PCM 82-17538 with the National Science Foundation and the University of California. The Government has certain rights in this invention.

This application is a continuation-in-part of application Ser. No. 690,679, filed Jan. 11, 1985 now abandoned.

FIELD OF THE INVENTION

The present invention relates generally to liposomes, and more particularly relates to a method of preserving liposomes containing biologically active, therapeutic or diagnostic agents. The process is useful in applications such as in vivo drug delivery and preservation of diagnostic agents prepared well before use.

BACKGROUND OF THE INVENTION

Liposomes are unilamellar or multilamellar lipid vesicles which enclose a fluid space. The walls of the vesicles are formed by a bimolecular layer of one or more lipid components having polar heads and non-polar tails. In an aqueous (or polar) solution, the polar heads of one layer orient outwardly to extend into the surrounding medium, and the non-polar tail portions of the lipids associate with each other, thus providing a polar surface and a non-polar core in the wall of the vesicle. Unilamellar liposomes have one such bimolecular layer, whereas multilamellar liposomes generally have a plurality of substantially concentric bimolecular layers.

A variety of methods for preparing liposomes are known, many of which have been described by Szoka and Papahadjopoulos, *Ann. Rev. Biophysics Bioeng.* 9:467–508 (1980). Also, several liposome encapsulation methods are disclosed in the patent literature, notably in U.S. Pat. Nos. 4,235,871, to Papahadjopoulos et al., issued Nov. 25, 1980, and in 4,016,100 to Suzuki et al., issued Apr. 5, 1977.

Liposomes are well recognized as useful for encapsulation of drugs and other therapeutic agents and for carrying these agents to in vivo sites. For example, U.S. Pat. No. 3,993,754, inventors Rahman et al., issued Nov. 23, 1976, discloses an improved chemotherapy method in which an anti-tumor drug is encapsulated within liposomes and then injected. U.S. Pat. No. 4,263,428, inventors Apple et al., issued Apr. 21, 1981, discloses an antitumor drug which may be more effectively delivered to selective cell sites in a mammalian organism by incorporating the drug within uniformly sized liposomes. Drug administration via liposomes can have reduced toxicity, altered tissue distribution, increased drug effectiveness, and an improved therapeutic index.

Although encapsulation of therapeutic agents and biologically active compounds in liposomes has significant commercial potential, a major difficulty that has been encountered in the commercial use of liposome encapsulates is with their long term stability.

Attempts have been made to preserve liposomes (and their encapsulated contents) by freeze-drying with various preserving agents, but the lyophilizates have lost a significant part of the encapsulated contents during the lyophilization and rehydration. U.S. Pat. No. 4,411,894, inventors Shrank et al., issued Oct. 25, 1983, discloses sonicated liposomes encapsulating fat-soluble pharmaceuticals which have a high sucrose concentration (at least 0.4 molar), and then the composition may be lyophilized. However, even at the pharmaceutically enormous amounts of sucrose disclosed by the Shrank et al. patent, there is still a significant loss of encapsulated contents (about 30%).

Crommelin et al., *Pharmaceutical Research*, pages 159–163 (1984) investigated the storage stability of liposomes when freeze-dried, frozen or as an aqueous dispersion. Crommelin et al. added lactose externally to liposomes, then froze and thawed the vesicles, but found the vesicles lost between 35 and 60% of the encapsulated contents. This loss was not decreased by the external addition of lactose.

SUMMARY OF THE INVENTION

It is an object of the present invention to provide a commercially and pharmaceutically acceptable method of preserving liposomes by means of freeze-drying, where resultant liposomes following rehydration can retain as much as 100% of their originally encapsulated material.

In one aspect of the present invention, a method for preserving liposomes includes freeze-drying liposomes having a size greater than about 30 nm and less than about 200 nm with a disaccharide preserving agent being present both internally with the encapsulated liposomal contents and externally. The encapsulated contents can include biologically active molecules, therapeutic agents and/or diagnostic agents. Suitable disaccharides are trehalose, sucrose, maltose and lactose. Trehalose is particularly preferred.

The lyophilizates so formed have a lipid component, a disaccharide component, and an encapsulated component, with the disaccharide component being present in a small amount admixed with the encapsulated component and the remaining disaccharide being present exterior the lipid membranes of the lyophilizates. The disaccharide component is in a weight ratio with respect to the lipid component of from at least about 0.1:1 to not greater than about 4:1. When reconstituted by rehydration, the resultant liposomes from the lyophilized composition retain up to 100% of the originally encapsulated component, or contents.

BRIEF DESCRIPTION OF THE DRAWINGS

In the drawings:

FIG. 1 is a graph illustrating uses of trehalose and sucrose respectively as the disaccharide preserving agent in accordance with the invention. The abscissa is the weight ratio of the particular sugar to lipid, and the ordinate is the percentage retention of encapsulated contents (with isocitric marker) following lyophilization and rehydration;

FIG. 2 is a graph illustrating the effect of vesicle size on the retention of encapsulated contents with trehalose as preserving agent, and with the abscissa and ordinate being as described for FIG. 1;

FIG. 3 is a electron micrograph taken by freeze-fracture, 80,000 magnification, showing freshly prepared liposomes of the invention with trehalose as the preserving agent and of about 50 nm size; and, FIG. 4 is a freeze-fracture electron micrograph of lyophilizates of the invention, 80,000 magnification, prepared from unilamellar vesicles analogous to those of FIG. 3.

DETAILED DESCRIPTION OF THE INVENTION

The invention comprises a method for preserving liposomes containing biologically active, therapeutic or diagnostic contents by freeze-drying liposomes in the presence of a preserving agent. The preserving agent is present internally as well as externally. Preferred preserving agents are carbohydrates having at least two monosaccharide units joined in glycosidic linkage, and particularly preferred preserving agents are sucrose, maltose, lactose and trehalose. Of these, trehalose has been found to be the most effective preserving agent for use with the inventive method, although maltose is quite good for particular encapsulates.

Trehalose is a naturally occurring sugar found at high concentrations in organisms capable of surviving dehydration. Trehalose is especially effective in preserving structure and function in dry biological membranes.

Liposomes which are freeze-dried in the presence of trehalose and which additionally contain encapsulated trehalose, exhibit excellent retention of encapsulates. That is, when liposomes are exposed to trehalose both internally and externally during freeze-drying, they can retain as much as 100% of their original encapsulated contents upon rehydration. This is in sharp contrast to liposomes which are freeze-dried without any preserving agent, which show extensive fusion between liposomes and loss of contents to the surrounding medium, and is in contrast to liposomes having a sugar present only externally, or only internally, during freeze-drying.

The present method reduces or eliminates the physical instability of liposomes during freeze-drying. Although prevention of vesicle fusion is believed necessary in reducing loss of liposomal contents during freeze-drying, it has been found to be not sufficient. The presence of the disaccharide internally and externally in the specified range of mass ratio with respect to lipid is believed to affect the lipid gel to liquid crystalline transition temperature during freezing so that the lipid membrane is not physically disrupted and does not leak the encapsulated contents.

Referring to FIG. 1, the graph shows that trehalose when present internally and externally provides increasing retention of encapsulated contents as a function of increasing trehalose to lipid ratios up to a value of about 4 g trehalose to 1 g lipid (about 0.05 M trehalose). Sucrose is shown in FIG. 1 as having a similar curve to trehalose, but is not as effective as trehalose. The FIG. 1 data are from rotary dried vesicles, the preparation of which will be described hereinafter. In other experiments, maltose has been found to be close to sucrose in retention and lactose to provide about 70% retention at a 1:1 mass ratio or greater. However, since maltose is a reducing sugar, it should not be used where there are free amino groups present. The FIG. 1 vesicles had a size of about 50 nm.

It has been discovered that vesicle size is a factor in retention of contents during freeze-drying and rehydration. FIG. 2 illustrates the percent retention of contents following freeze-drying and rehydration for vesicles of a size 200 nm, 100 nm, 50 nm and 25 nm, respectively, prior to freeze-drying. A preferred vesicle size about range is from about 50 nm to about 150 nm, more preferably an average of about 50 to 100 nm and is preferably achieved by extruding the vesicles through polycarbonate membranes before freeze-drying. Rotary drying also gives vesicles having a size about 50 nm. Both trehalose and sucrose provide optimal stability at the lowest sugar concentration when the vesicles are about 50 nm in diameter. Smaller vesicles are much less stable. However, larger vesicles (ca. 100 nm in diameter) are about as stable as those 50 nm in diameter if slightly more trehalose or sucrose is used during the lyophilization. Loss in stability occurs somewhere between 100 and 200 nm in diameter.

Representative phospholipids used in forming liposomes which may be used in this process include phosphatidylcholine, phosphatidylserine, phosphatidic acid and mixtures thereof. Even lipids that have been found to hydrogen bond directly to each other during freeze-drying, such as phosphatidyl ethanolamine, may be used with the invention. Both natural and synthetic phospholipids may be successfully used. The particular lipid or lipid mixture used in forming the liposomes has been found to affect the amount of disaccharide best used within a 0.1:1 and 4:1 range. (A 4:1 disaccharide to lipid dry mass ratio is comparable to 50 mM of sugar).

Suitable lipids include both naturally occurring and synthetically prepared phosphatidylcholine ("PC"), phosphatidic acid ("PA"), phosphatidylserine ("PS"), phosphatidylethanolamine ("PE"), sphingolipids, phosphatidylglycerol ("PG"), spingomyelin, cardiolipin, glycolipids, gangliosides, cerebrosides and the like used either singularly or intermixed. Illustrative lipids are soybean phospholipids, egg phosphatidylcholine ("EPC"), dilauryloylphosphatidylcholine ("DLPC"), dimyristoylphosphatidylcholine ("DOPC"), dipalmitoylphosphatidylcholine ("DPPC"), distearoylphosphatidylcholine ("DSPC"), 1-myristoyl-2palmitoyl-phosphatidylcholine ("MPPC"), 1-palmitoyl-2myristoyl phosphatidylcholine ("PMPC"), 1-palmitoyl-2-stearoyl phosphatidylcholine ("PSPC"), 1-stearoyl-2-palmitoyl phosphatidylcholine ("SPPC"), dioleoyl-phosphatidylycholine ("DOPC"), dilauryloylphosphatidylglycerol ("DLPG"), dimyristolphosphatidylglycerol ("DMPG"), dipalmitoylphosphatidylglycerol ("DPPG"), distearoylphosphatidylglycerol ("DSPG"), dioleoylphosphatidylglycerol ("DOPG"), dimyristoyl phosphatidic acid ("DMPA"), dipalmitoyl phosphatidic acid ("DPPA"), dimyristoyl phosphatidylethanolamine ("DMPE"), dipalmitoyl phosphatidylethanolamine ("DPPE"), other PE species, dimyristoyl phosphatidylserine ("DMPS"), dipalmitoyl phosphatidylserine ("DPPS"), brain phosphatidylserine ("PS"), brain sphingomyelin ("BSP"), dipalmitoyl sphingomyelin ("DPSP"), and distearoyl sphinmyelin ("DSSP").

Particularly preferred lipids and lipid mixtures include egg phosphatidylcholine, palmitoyloleoyl phosphatidylcholine and phosphatidylserine, or phosphatidylcholine and phosphatidic acid. These lipid/lipid mixtures have lower transition temperatures (are more fluid at room temperature) and are best preserved during freeze-drying and rehydration when the mass ratio of disaccharide to lipid is between about 1:1 to about 2:1.

As illustrated by comparing FIG. 3 with the lyophilizates of FIG. 4, even when freeze-dried the inventive lyophilizates continue to define lipid membranes. The encapsulated contents, including a small portion of the disaccharide, are interior to the membranes.

The biologically active or therapeutic encapsulated material is preferably water soluble. Examples of suitable therapeutic agents with which this preservation method can successfully be carried out include sympathomimetic drugs such as amphetamine sulfate, epinephrine hydrochloride, or ephedrine hydrochloride; antispasmodics such as atropine or scopalamine; bronchodilators such as isoproternol; vasodilators such as dilthiazen; hormones such as insulin; and antineoplastic drugs such as adriamycin. Suitable biologically active molecules include, for example, RNA, DNA, enzymes and immunoglobulins. In addition, the encapsulated contents can include diagnostic agents such as radioactive ions, fluorescers, chemiluminescent molecules, and the like.

Since the disaccharide is present on both sides of the phospholipid bilayer, or liposomal membrane, methods of preparing the vesicles with the disaccharide trapped internally before freeze-drying are necessary (and the disaccharide is added externally before freeze-drying). Because vesicle size has been found to be an important factor, methods that produce a relatively homogeneous size distribution of the desired size are preferred. Such methods include sequential extrusion through polycarbonate filters (described in U.S. Pat. No. 4,529,561, issued July 16, 1985, inventors Hunt and Papahadjopoulos) or rotary drying (U.S. Pat. No. 4,515,730, inventor Deamer, issued May 7, 1985).

The vesicles having entrapped disaccharide and external disaccharide are then frozen, such as in liquid nitrogen, and lyophilized. Under some circumstances, as when lipids are used which are susceptible to oxidative damage, or chemical instability, due to the presence of oxygen, it may be desirable to seal the dry preparations under vacuum. Rehydration is accomplished simply by adding water to the lyophilizates.

Multilamellar vesicles (MLV's) or small unilamellar vesicles (SUV's) may be prepared as starting materials for the inventive method by any of the available techniques. Suitable techniques include dispersion of the dry lipid in water and sonication.

Larger unilamellar vesicles (LUV's) with increased trapping efficiency may be prepared from SUV's made by sonication by either freeze-thawing or rotary evaporation. Rotary evaporation results in vesicles roughly about 50 nm in size. An exemplary rotary evaporation method and one which is especially effective in conjunction with the method disclosed herein is illustrated in Deamer, D.W., "A Novel Method for Encapsulation of Macromolecules in Liposomes" in Gregoriadis, G. (ed.) *Liposome Technology* (1984). The method comprises providing a polar solution having initial liposomes and a quantity of material to be encapsulated along with the stabilizing sugar. Substantially all of the solution is removed, and the resultant liposomes are then recovered by hydration of the concentrated admixture. This method is also the subject of U.S. Pat. No. 4,515,736, inventor Deamer, et al., issued May 7, 1985. The resulting vesicles may then be made more uniform by filtration, centrifugation or gel permeation chromatography.

If the final vesicles are to be prepared by extrusion through polycarbonate filters, MLV's are prepared in the presence of the material to be trapped and in the presence of the stabilizing sugar. These vesicles are then extruded through suitable polycarbonate filters, producing unilamellar vesicles with the desired material and sugar trapped inside.

Examples 1-5 below are of liposomes prepared first by sonication and next by either rotary drying or freeze-thawing. Freeze-thawing is no longer a preferred method of practicing the invention. A particularly preferred means of preparing the initial liposomes, ready for freezing, is illustrated by Example 7(c). Example 7(c) illustrates a different means of preparation in which multilamellar vesicles (MLV's) are first simply prepared by suspending the lipid component in water, next freeze-thawing the MLV's (preferably about five times), and then extruding through successively smaller orifice polycarbonate membranes. During the extrusion step, disaccharide is added and some (about 0.05 g/g lipid) is trapped inside the extruded liposomes. The extruded liposomes are of a substantially homogeneous size. The Example 7(c) preparation is particularly preferred because it produces liposomes having a relatively homogeneous size of about 50 nm.

The following examples illustrate certain aspects and embodiments of the present invention, and are not intended to limit the scope of the invention as defined in the appended claims.

EXAMPLE 1

A phospholipid mixture consisting of approximately 40 mg dipalmitoyl phosphatidylcholine and phosphatidic acid in a molar ratio of 95:5 was sonicated to optical clarity in a bath sonicator. Large unilamellar vesicles were prepared by freeze-thawing in a 50 mM solution of isocitric acid in water as the compound to be encapsulated. Excess isocitric acid was removed by dialysis. Trehalose (2.0:1.0 trehalose:phospholipid weight ratio) was added either after freeze-thawing, beforehand or not at all, thus providing some large unilamellar vesicles with external trehalose only, some with internal trehalose only, and some vesicles with trehalose both externally and internally.

Isocitric acid was assayed by adding isocitrate dehydrogenase and NADP to the outside of the vesicles according to the method of Plaut, et al. (Eds.), *Methods in Enzymology*, Volume 5 (New York: Academic Press). Isocitrate external to the vesicles was oxidized by the isocitrate dehydrogenase, resulting in reduction of NADP to NADPH, the rate and amount of which may be recorded fluorometrically. Total isocitric acid in the vesicles was assayed following addition of Triton X-100 (octylphenoxy polyethoxyethanol, a detergent and emulsifier manufactured by Rohm & Haas Co., Philadelphia, PA; "TRITON" is a registered trademark of Rohm & Haas Co.), which releases the trapped isocitric acid into the surrounding medium. Isocitric acid trapped in the vesicles was assayed before and after both lyophilization and rehydration, thus providing an estimate of the efficiency with which the trapped isocitrate was retained.

As may be seen in Table 1, the results show that over sixty percent (60%) of the trapped isocitrate was retained when the vesicles were lyophilized with trehalose both inside and outside the vesicles. When trehalose was present externally only, there was still an increase in the efficiency of retention, but to a much lesser degree than in the case where trehalose was present on both sides of the lipid membrane. When trehalose was present internally only, there was no increase in retention. Examination of lipid concentration at time of freezing showed that such had no significant effect on retention of trapped material following lyophilization.

TABLE 1

| Method of Preparing Vesicles | Concentration of Lipid (mg/ml) | g Trehalose /g Lipid | Trehalose External | Trehalose Internal | % Retention |
|---|---|---|---|---|---|
| FT* | 10.8 | 0 | — | — | 0 |
| FT | 11.1 | 0.08 | — | + | 0 |
| FT | 10.8 | 1.78 | + | — | 42 |
| FT | 11.1 | 1.78 | + | + | 61 |

*FT = freeze-thaw

While the above-described sonication and then freeze-thawing method may be utilized, when the preferred alternative methods of rotary drying or extrusion of the invention are utilized, then superior results are obtained as illustrated by Examples 2, 3, 5 and 6.

EXAMPLE 2

Small unilamellar vesicles were made by sonication of 43 mg egg phosphatidycholine in 4 ml of water. Large unilamellar vesicles were then prepared by rotary drying the phospholipid in the presence of 32 mg of trehalose and 13 mg of isocitric acid. The weight ratios of phospholipid:trehalose:isocitric acid were approximately 4:3:1. Excess isocitric acid and trehalose were removed by dialysis against distilled water, and the amount of isocitric acid trapped in the vesicles was determined by the enzyme assay described in Example 1. Trehalose was added to the dialyzed liposomes to give a final weight ratio of phospholipid:trehalose of 1.0:1.4, and the sample was lyophilized. The sample was then rehydrated with distilled water, and the amount of isocitric acid remaining in the liposomes was determined by enzyme assay. The lyophilized vesicles retained 75% of their original contents.

EXAMPLE 3

A phospholipid mixture of palmitoyloleoyl phosphatidylcholine (90%) and phosphatidylserine (10%) was hydrated to 10 mg./ml., and small unilamellar vesicles were then prepared by sonication. Unilamellar vesicles were prepared by rotary drying in the presence of isocitric acid, which served as the encapsulated molecule. Essentially the same techniques as previously described in Examples 1 and 2 were used. Efficiency of retention of isocitric acid following lyophilization and rehydration was recorded as before, with unilamellar vesicles approximately 50 nm in diameter lyophilized first in the presence and then in the absence of trehalose. As may be seen in Table 2, the results show that 100% of the trapped isocitric acid is retained when the large unilamellar vesicles are lyophilized and rehydrated under the stated conditions. As the previous examples demonstrated, trehalose should be present both externally and internally to optimize retention of the encapsulate.

TABLE 2

| Method of Preparing Vesicles | g Trehalose /g Lipid | Trehalose External | Trehalose Internal | % Retention |
|---|---|---|---|---|
| RD* | 0.06 | — | + | 0 |
| RD | 3.2 | + | + | 100 |
| RD | 0 | — | — | 0 |
| RD** | 3.9 | + | — | 26 |
| RD | 0.11 | + | + | 22 |
| RD | 0.19 | + | + | 49 |
| RD | 0.33 | + | + | 69 |
| RD | 0.63 | + | + | 76 |
| RD | 0.91 | + | + | 86 |
| RD | 1.76 | + | + | 99 |

*RD = rotary drying
**The lipid was rotary dried and the resulting vesicles were sized by gel filtration to produce vesicles approximately the same size as those used for measurements without trehalose.

EXAMPLE 4

One of the damaging events presumed to be occurring during lyophilization is close approach of the large unilamellar vesicles to each other, leading to fusion and leakage of the vesicular contents. Fusion has been assayed by resonance energy transfer, a fluorescence method which depends upon energy transfer from an excited probe (the "donor probe") to a second probe (the "acceptor probe"). The acceptor probe fluoresces when the energy transfer occurs. In order for the transfer to occur the two probes must be in close proximity. Thus probe intermixing can be used as an assay for fusion between vesicles during lyophilization. Unilamellar vesicles (about 50 nm in diameter) were prepared with donor probe in one preparation and acceptor probe in another, and the two preparations were mixed before lyophilization. Following lyophilization and rehydration, probe intermixing was measured, with the results listed in Table 3. The results show that with increasing trehalose concentration there is a decrease in probe intermixing. Thus, use of trehalose tends to reduce fusion of the vesicles.

TABLE 3

| Method of Preparing Vesicles | g Trehalose /g Lipid | Trehalose External | Trehalose Internal | % Probe Mixing |
|---|---|---|---|---|
| RD* | 0.05 | — | + | 72 |
| RD | 0.15 | + | + | 39 |
| RD | 0.25 | + | + | 29 |
| RD | 0.50 | + | + | 12 |
| RD | 0.95 | + | + | 8 |
| FT** | 0 | — | — | 93.0 |
| FT | 0.4 | + | + | 79.0 |
| FT | 0.8 | + | + | 59.0 |
| FT | 1.2 | + | + | 54.0 |
| FT | 1.6 | + | + | 38.0 |
| FT | 2.0 | + | + | 15.0 |

*RD = rotary drying
**FT = freeze-thaw

EXAMPLE 5

A further experiment was carried out identical to that set forth in Example 3, with first maltose and then sucrose as the preserving agent. Results are set forth in Tables 4 and 5. As may be concluded from those tables, both maltose and sucrose provide good retention of encapsulated material following lyophilization when the respective sugar was present both internally and externally.

TABLE 4

| Method of Preparing Vesicles | g Maltose /g Lipid | Maltose External | Maltose Internal | % Retention |
|---|---|---|---|---|
| RD | 0.05 | — | + | 3 |
| RD | 0.15 | + | + | 41 |
| RD | 0.25 | + | + | 88 |
| RD | 0.49 | + | + | 95 |

TABLE 4-continued

| Method of Preparing Vesicles | g Maltose /g Lipid | Maltose External | Internal | % Retention |
|---|---|---|---|---|
| RD | 0.64 | + | + | 100 |

TABLE 5

| Method of Preparing Vesicles | g Sucrose /g Lipid | Sucrose External | Internal | % Retention |
|---|---|---|---|---|
| RD | 0.07 | − | + | 20 |
| RD | 0.35 | + | + | 57 |
| RD | 0.49 | + | + | 89 |
| RD | 0.83 | + | + | 86 |
| RD | 1.15 | + | + | 91 |

EXAMPLE 6

The data illustrated by FIG. 1 were obtained from three groups of preparations of liposomes in accordance with the invention. The preparations were as described by Example 3. One group had trehalose as the preserving agent, and another had sucrose.

EXAMPLE 7

Twelve preparations of liposomes (six for each of trehalose and sucrose) were prepared. The trehalose data is shown by FIG. 2. The FIG. 3 and FIG. 4 data micrographs were taken from the 50 nm trehalose description. These preparations are described as follows.

25 nm or 30 nm vesicles, trehalose (a) Small unilamellar vesicles composed of egg phosphatidylcholine (90%) and bovine brain phosphatidylserine (10%) were created in the following way. The two lipids were mixed in chloroform, and the chloroform removed by evaporation. The dry lipids were then dispersed (20 mg lipid/ml solution) in water containing 0.5 M trehalose and 0.2 M carboxyfluorescein. The latter compound is a fluorescent marker that is self-quenching at high concentrations. When it is trapped in the liposomes at 0.2 M it fluoresces weakly, and the fluorescence increases when it leaks into the surrounding medium. The vesicles were sonicated, and following sonication the excess trehalose and carboxyfluorescein were removed by gel filtration. Trehalose was added to the vesicles to produce the desired dry mass ratio of trehalose to lipid, after which the vesicles were lyophilized. After rehydration the fluorescence in the medium surrounding the vesicles was recorded. The vesicles were then lysed by addition of 20 μL 1% Triton X-100 and the fluorescence resulting from release of trapped carboxyfluorescein was recorded. The results showed that small unilamellar vesicles dried with trehalose retained about 70% of trapped CF at a mass ratio of about 8 g trehalose/g lipid. At 4 g trehalose/1 g lipid, retention was only about 45% (FIG. 2).

(b) For comparison with the sonicated vesicles described above, vesicles approximately 30 nm in diameter were prepared by extrusion through polycarbonate filters with 30 nm pore size as follows. Egg phosphatidylcholine (90%) and bovine phosphatidylserine (10%) were mixed in chloroform and the chloroform was evaporated to dryness. The dry lipids were then dispersed in water containing 0.5 M trehalose and 0.2 M carboxyfluorescein (CF). The resulting multilamellar vesicles were then freeze-thawed five times by immersion in liquid nitrogen, followed by thawing in a water bath at 40° C. The vesicles were then passed successively through polycarbonate filters with 400 nm, 200 nm, 100 nm, 50 nm, and 30 nm pore sizes, with five passes through each filter. Excess trehalose and CF were removed from the resulting small vesicles by gel filtration, after which trehalose was added to the vesicles to produce the desired mass ratio of trehalose to lipid. The vesicles were then lyophilized. Retention of trapped CF was recorded in the rehydrated vesicles. The results show that these 30 nm vesicles prepared by extrusion are closely comparable in their stability to sonicated vesicles.

50 nm vesicles, trehalose (c) Vesicles approximately 50 nm in diameter were prepared by extrusion through polycarbonate filters as described in (b), above, except that the vesicles were not passed through the final filter in the series (30 nm). The results show that when these vesicles are in a mass ratio of about 2 g trehalose to 1 g lipid, then they are remarkably stable, retaining up to 100% of the trapped CF following lyophilization (FIG. 2).

100 nm vesicles, trehalose

Vesicles approximately 100 nm in diameter were prepared by extrusion through polycarbonate filters as described in (b), above, except that the vesicles were passed through the series of filters only to the 100 nm stage. The results show that, like the 50 nm vesicles, these vesicles are remarkably stable, retaining up to 100% of the trapped CF following lyophilization (FIG. 2). However, somewhat more trehalose is required to achieve this level of stabilization than that required for 50 nm vesicles.

200 nm vesicles, trehalose

Vesicles approximately 200 nm in diameter were prepared by extrusion through polycarbonate filters as described in (b), above, except that the vesicles were passed through the series of filters only to the 200 nm stage. The results show that, unlike the 50 nm and 100 nm vesicles, these vesicles are considerably less stable, retaining only about 40% of the trapped CF following lyophilization in the presence of 4 g trehalose/g lipid (FIG. 2).

Large unilamellar vesicles, trehalose

Large unilamellar vesicles were prepared by extrusion through polycarbonate filters as described above, except that the vesicles were passed only through the 400 nm filter. Freeze fracture of these preparations indicated that they were heterogeneous with respect to vesicle size, very large vesicles on the order of 400 nm in diameter and a considerable number of smaller ones both present. When these vesicles were lyophilized and rehydrated, the results show that these vesicles are considerably less stable than the 50 or 100 nm vesicles, retaining only about 40% of the trapped CF following lyophlization in the presence of 4 g trehalose/g lipid. These vesicles are therefore very similar in their stability to the 200 nm vesicles.

25 nm or 30 nm vesicles, sucrose

Small unilamellar vesicles created by sonication (shown by freeze fracture to be about 25 nm in diameter) were prepared and lyophilized in the presence of sucrose exactly as described in Example 7(a). The results show that such vesicles are very unstable, retaining only about 10% of the trapped CF, even when lyophilized with 4 g sucrose/g lipid.

Vesicles about 30 nm in diameter were prepared by extrusion through polycarbonate filters exactly as described in (b), above, except that sucrose was used instead of trehalose. The results show that such vesicles are similar to sonicated vesicles in their stability.

50 nm vesicles, sucrose

Vesicles about 50 nm in diameter were prepared by extrusion through polycarbonate filters exactly as described in (b), above, except that sucrose was used instead of trehalose. The results show that such vesicles are very stable during lyophilization, achieving greater than 90% retention of trapped CF when lyophilized in the presence of as little as 1 g sucrose/g lipid.

100 nm vesicles, sucrose

Vesicles about 100 nm in diameter were prepared by extrusion through polycarbonate filters exactly as described in (b), above, except that sucrose was used instead of trehalose. The results show that such vesicles are very stable during lyophilization, achieving greater than 90% retention of trapped CF when lyophilized in the presence of as little as 2 g sucrose/g lipid.

200 nm vesicles, sucrose

Vesicles about 200 nm in diameter were prepared by extrusion through polycarbonate filters exactly as described in (b), above, except that sucrose was used instead of trehalose. The results show that such vesicles are considerably less stable during lyophilization than the smaller ones, achieving only about 40% retention of trapped CF when lyophilized in the presence of as much as 4 g sucrose/g lipid.

Large unilamellar vesicles, sucrose

Large unilamellar vesicles were prepared by extrusion through polycarbonate filters exactly as described in (b), above, except that the vesicles were passed only through the 400 nm filter. Freeze fracture of these preparations indicated that they were heterogeneous with respect to vesicle size, very large vesicles on the order of 400 nm in diameter and a considerable number of smaller ones both present. When these vesicles were lyophilized and rehydrated, the results show that these vesicles are considerably less stable than the 50 or 100 nm vesicles, retaining only about 40% of the trapped CF following lyophilization in the presence of 4 g sucrose/g lipid. These vesicles are therefore very similar in their stability to the 200 nm vesicles.

Both trehalose and sucrose provide optimal stability at the lowest sugar concentration when the vesicles are about 50 nm in diameter. Smaller vesicles are much less stable. However, larger vesicles (ca. 100 nm in diameter) are about as stable as those 50 nm in diameter, if slightly more trehalose or sucrose is used during the lyophilization. Loss in stability occurs somewhere between 100 and 200 nm in diameter.

EXAMPLE 8

Phosphatidylethanolamines (PE's) are often used in preparation of phospholipid vesicles for commercial preparations. This lipid presents special problems in its preservation in that it tends to enter the non-bilayer hexagonal phase when it is dried. This phase is clearly incompatible with the maintenance of low permeability, and such vesicles would leak their contents to the medium. However, trehalose can stabilize PE's in bilayers under conditions when they would normally be in hexagonal phase, as the following experiments indicate.

Dioleoyl-PE was dispersed from a dry powder in water and vortexed. The lipid was dried on an electron microscope grid in the presence of phosphotungstic acid, which provides a negative stain that can be used to visualize the phospholipid structure. When trehalose (2 moles trehalose/mole lipid) was added before drying, an image of multilamellar structure was obtained. Without trehalose, an image representing the non-bilayer, hexagonal phase was obtained.

Similar experiments to those described above were done with freeze-fracture to detect the presence of hexagonal phase lipids. For these experiments PE derived from soybeans were dispersed in water and vortexed either in the presence or absence of trehalose. The lipids were then heated to 40° C. (a temperature at which they should be in hexagonal phase), frozen rapidly between thin copper plates in liquid freon, and freeze-fractured. The results show that when lipids were frozen in the presence of trehalose, they were seen to exist as lamellar structures. In the absence of trehalose, however, they were seen to have undergone a phase transition to hexagonal phase.

EXAMPLE 9

SUV's of egg PC (90%) and PS (10%) were prepared exactly as described in Example 7(a) except that the vesicles were sonicated in the presence of trehalose by concentrations up to about 80 g trehalose to 1 g/lipid (about 1 M sugar). In adding the trehalose, the medium in which the vesicles were sonicated contained 0.2 M CF as a marker. After sonication the excess trehalose and CF were removed by gel filtration. Sufficient trehalose was then added to one batch of vesicles to produce the desired mass ratio. Both batches of vesicles were then lyophilized, rehydrated, and the retention of CF was determined. At all mass ratios of trehalose to lipid used there was a large difference between the curves of vesicles prepared with trehalose both internal and external and with vesicles prepared on the outside only. This shows that altering the internal concentration of the sugar has little or no effect on vesicle stability. In other words, the effect of adding trehalose both internally and externally prior to freeze-drying is not simply additive with respect to adding trehalose only externally and adding trehalose only internally.

While the invention has been described in connection with specific embodiments thereof, it will be understood that it is capable of further modifications, and this application is intended to cover any variations, uses or adaptations of the invention following, in general, the principles of the invention and including such departures from the disclosure as come within the known or customary practice in the art to which the invention pertains and as may be applied to the essential features hereinbefore set forth, and as fall within the scope of the invention and the limits of the appended claims.

I claim:
1. A preserved liposomal composition comprising;
   lyophilizates defining lipid vesicles having an average size of from about 50 nm to about 100 nm, an initial quantity of material being encapsulated by the vesicles, and a disaccharide component being present both interior and exterior to the lipid vesicles, and the disaccharide component being from about 0.1:1 to about 4:1 with respect to the lipid component.

2. The composition as in claim 1 wherein the encapsulated material includes a water-soluble therapeutic agent, a biologically active compound, or a diagnostic agent.

3. The composition as in claim 1 or 2 wherein the disaccharide component is trehalose, maltose, lactose or sucrose.

4. The composition as in claim 3 wherein the lyophilizates are rehydratable with sufficient water as resultant liposomes and the resultant liposomes encapsulate at least about 80% to about 100% of the initial quantity of encapsulated material.

5. The composition as in claim 4 wherein the rehydrated liposomes are about 50 nm in diameter.

6. The composition as in claim 1 wherein the disaccharide preserving agent is trehalose in an amount of from about 1:1 to about 4:1 with respect to the lipid component, and the lipid vesicles of the lyophilizates have a size of about 50 nm.

7. A method for preserving liposomes, comprising:
providing initial liposomes formed from one or more lipids and having an average size from about 50 nm to about 100 nm, the initial liposomes encapsulating an initial quantity of biologically active, therapeutic or diagnostic material and a disaccharide preserving agent;
contacting said initial liposome with more of the disaccharide preserving agent in an aqueous solution, the total disaccharide preserving agent being in a weight ratio with respect to lipid from about 0.1:1 to about 4:1; and
lyophilizing said initial liposome in the presence of the preserving agent to form lyophilizates.

8. The method as in claim 7, further comprising recovering resultant liposomes from said lyophilizates by adding an aqueous solution to said lyophilizates, the resultant liposomes encapsulating at least about 80 wt. % of said initial quantity of encapsulated material.

9. The method as in claim 7 or 8 wherein the disaccharide preserving agent is trehalose, maltose, lactose, or sucrose.

10. The method as in claim 8 wherein the resultant liposomes encapsulate up to 100% of said initial quantity of encapsulated material, and the disaccharide preserving agent is trehalose.

11. The method as in claim 7 or 10 further comprising extruding the initial liposomes before the lyophilizing to a relatively homogeneous size of about 50 nm.

12. A liposomal composition comprising:
a plurality of liposomes having an average size from about 50 nm to about 100 nm, an initial quantity of material being encapsulated by the liposomes, the liposomes dispersed in a solution, the initial quantity of material and the solution each having a disaccharide component therein, the disaccharide component being from about 0.1:1 to about 4:1 with respect to a lipid component of the liposome.

13. The liposomal composition as in claim 12 wherein the disaccharide component is trehalose, maltose, lactose or sucrose.

14. The liposomal composition as in claim 12 wherein the disaccharide component is trehalose.

* * * * *